(12) United States Patent
Jenkins (10) Patent No.: US 9,786,261 B2
(45) Date of Patent: Oct. 10, 2017

(54) ACTIVE NOISE REDUCTION EARCUP WITH SPEAKER ARRAY

(71) Applicant: Honeywell International Inc., Morristown, NJ (US)

(72) Inventor: John Jenkins, San Diego, CA (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/571,031

(22) Filed: Dec. 15, 2014

(65) Prior Publication Data

US 2016/0171962 A1    Jun. 16, 2016

(51) Int. Cl.
*H04R 1/00* (2006.01)
*G10K 11/16* (2006.01)
*H04R 3/00* (2006.01)
*G10K 11/175* (2006.01)
*H04R 1/10* (2006.01)
(Continued)

(52) U.S. Cl.
CPC ............ *G10K 11/175* (2013.01); *A61F 11/14* (2013.01); *H04R 1/1083* (2013.01); *G10K 2210/1081* (2013.01); *H04R 3/12* (2013.01); *H04R 2430/03* (2013.01); *H04R 2460/01* (2013.01)

(58) Field of Classification Search
CPC .. H04R 2430/01; H04R 2430/03; H04R 1/24; H04R 1/26; H04R 1/403; H04R 1/1083; H04R 2460/01; H04R 3/04; H04R 3/12; H04R 2205/022; H04R 2205/024; H04R 29/002; H04R 2201/403; H04R 2201/405; H04S 7/307; G10L 21/0208; G10K 11/175; G10K 2210/1081; H04M 9/082
See application file for complete search history.

(56) References Cited

U.S. PATENT DOCUMENTS 3,984,885 A * 10/1976 Yoshimura ............ H04R 5/033
                                                          381/19
5,675,658 A * 10/1997 Brittain .................... A61F 11/14
                                                          381/186

(Continued)

FOREIGN PATENT DOCUMENTS

KR    20050088575 A     9/2005
KR    20070110985 A    11/2007
(Continued)

OTHER PUBLICATIONS

PCT Application No. PCT/US2015/064382, International Search Report, dated May 4, 2016, 4 pages.

(Continued)

*Primary Examiner* — Thang Tran
(74) *Attorney, Agent, or Firm* — Conley Rose, P.C.; Kristin Jordan Harkins (57) ABSTRACT

Embodiments relate generally to devices and methods for improved active noise cancellation hearing protection. For example, multiple speakers might be used in each earcup, with each speaker providing active noise cancellation for a narrow frequency range which is a portion of the total frequency range of the entire array of speakers. By dividing the active noise cancellation up across an array of speakers, each speaker can better target its specific narrow frequency range, resulting in improved active noise cancellation.

18 Claims, 3 Drawing Sheets

(51) Int. Cl.
*A61F 11/14* (2006.01)
*H04R 3/12* (2006.01)

(56) References Cited

U.S. PATENT DOCUMENTS

| | | | |
|---|---|---|---|
| 8,891,798 B1* | 11/2014 | Laffon de Mazieres | H04R 1/1033 381/370 |
| 2006/0008094 A1* | 1/2006 | Huang | H04S 3/008 381/79 |
| 2006/0204016 A1* | 9/2006 | Pham | H04R 1/1075 381/74 |
| 2007/0195984 A1* | 8/2007 | Yang | H04R 1/1075 381/372 |
| 2009/0175463 A1* | 7/2009 | Lee | H04R 3/005 381/71.6 |
| 2011/0081036 A1 | 4/2011 | Brown | |
| 2011/0158440 A1 | 6/2011 | Mei et al. | |
| 2012/0259626 A1 | 10/2012 | Li et al. | |
| 2014/0270222 A1 | 9/2014 | Hendrix et al. | |

FOREIGN PATENT DOCUMENTS

| | | |
|---|---|---|
| WO | 2004040941 A1 | 5/2004 |
| WO | 2006/008492 A2 | 1/2006 |
| WO | 2014/100573 A2 | 6/2014 |

OTHER PUBLICATIONS

PCT Application No. PCT/US2015/064382, Written Opinion, dated May 4, 2016, 7 pages.

\* cited by examiner

ACTIVE NOISE REDUCTION EARCUP WITH SPEAKER ARRAY

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

FIELD

Embodiments may relate generally to devices and/or methods for improved active noise reduction (e.g. for hearing protection devices).

BACKGROUND

Typical active noise reduction systems use a single speaker for each ear, with the single speaker then being required to reproduce the active noise cancellation signal (for example, in order to protect the user from external sound/noise in the environment). Such typical active noise cancellation systems tend to have relatively poor performance in certain portions of the frequency range of human hearing. For example, typical active noise reduction systems tend to perform poorly at cancelling low frequencies. The present embodiments seek to provide improved active noise cancellation, for example better cancelling sound/noise across the entire frequency range.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field (for example, +/−10%); and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Figure 1:
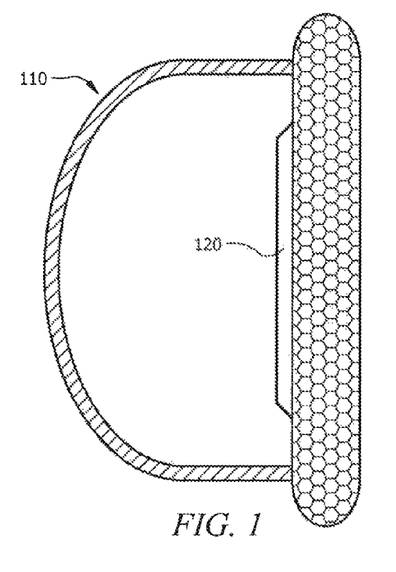
FIG. 1 illustrates schematically a cross-section of an embodiment of a typical/conventional active noise reduction earcup.

Conventional active noise cancellation earmuffs typically have a single speaker 120 per earcup 110, as shown in FIG. 1 for example, in order to transmit the noise cancellation sound waves into the user's ear canal. However, such typical/conventional active noise cancellation systems tend to have relatively poor performance in certain portions of the frequency range of human hearing. For example, typical active noise reduction systems tend to perform poorly at cancelling low frequencies and/or may be focused on the middle frequency ranges (while not covering the uppermost and bottommost frequency ranges, or providing reduced protection for these ranges). Disclosed embodiments may be designed to address such issues.

So, the disclosed embodiments may generally relate to an improved device (for example earmuffs, headphones, or earcup(s) for such devices) for active noise cancellation. Typically, such disclosed headphones or earmuffs might include two earcups (one for each ear). For example, such a device might comprise a hollow earcup (e.g. a hollow cup shell or body) operable to enclose (the entrance to) a user's ear canal and to provide passive noise reduction, and an array of speakers within the earcup, with the array of speakers providing active noise cancellation over a total frequency range, the array of speakers comprising a plurality of speakers, and each speaker providing active noise cancellation for a narrow frequency range which is a portion of the total frequency range (which, for example, might be related to the external noise/sound to be cancelled and/or the output signal from active noise cancellation circuitry and/or the range of human hearing). While the total frequency range (for which the speaker array provides active noise cancellation) might be any range of frequencies (for example, based on the expected exposure in the particular environment), in some embodiments the total frequency range might cover approximately the entire range of human hearing (e.g. approximately 20 Hz to 20 kHz).

Typically, each of the plurality of speakers may be configured to maximize reproduction within its corresponding narrow frequency range (allowing each speaker to be better focused on sound quality reproduction in the narrow range, as opposed to use of a single speaker to cover the entire/total frequency range, which would lead to some frequencies being poorly addressed due to the limitations of such a single speaker). In several embodiments, the plurality of speakers may comprise speakers of varying sizes and resonant frequencies (e.g. to better attune each speaker to its specific, corresponding narrow frequency range). For example, at least one of the plurality of speakers may be a 40-50 mm speaker with a narrow frequency range corresponding to the bottom portion of the total frequency range, and at least one of the plurality of speakers may be a 5 mm speaker with a narrow frequency range corresponding to the uppermost portion of the total frequency range. For example, in an embodiment each earcup might have three speakers (for a total of six speakers in the headset), with a 5 mm speaker for frequencies of 10,000 Hz to 15,000 Hz, a 15-20 mm speaker for frequencies of 3,000 Hz to 10,000 Hz, and a 40-50 mm speaker for frequencies of 20 Hz to 3,000 Hz.

Typically, the device would also include elements for producing the active noise reduction signal for the speaker array in the earcup (although in other embodiments, the earcup could be a separate device which would be operable for use with a separate active noise cancellation system). So for example, such an embodiment might further comprise an external microphone operable to detect noise external to the earcup; and active noise cancellation circuitry, with the active noise cancellation/reduction circuitry receiving a signal for detected external noise from the external microphone, and then generating an output signal for active noise cancellation based on the detected external noise. Typically, the active noise cancellation circuitry would generate the output signal for active noise cancellation by inversion of the detected external noise from the external microphone, for example. In some embodiments, the active noise cancellation circuitry would also divide the resulting active noise cancellation output signal into frequency range bands for transmission to corresponding speakers, with each frequency range band corresponding to a specific speaker having a corresponding narrow frequency range (although in other embodiments, this functionality might be provided by one or more separate elements, for example if the earcups are configured for use with an off-the-self (separate and apart) active noise cancellation system). So for example, the active noise reduction circuitry (and/or the additional elements of the device) might include one frequency filter for each speaker and/or one amplifier for each speaker.

Figure 3:
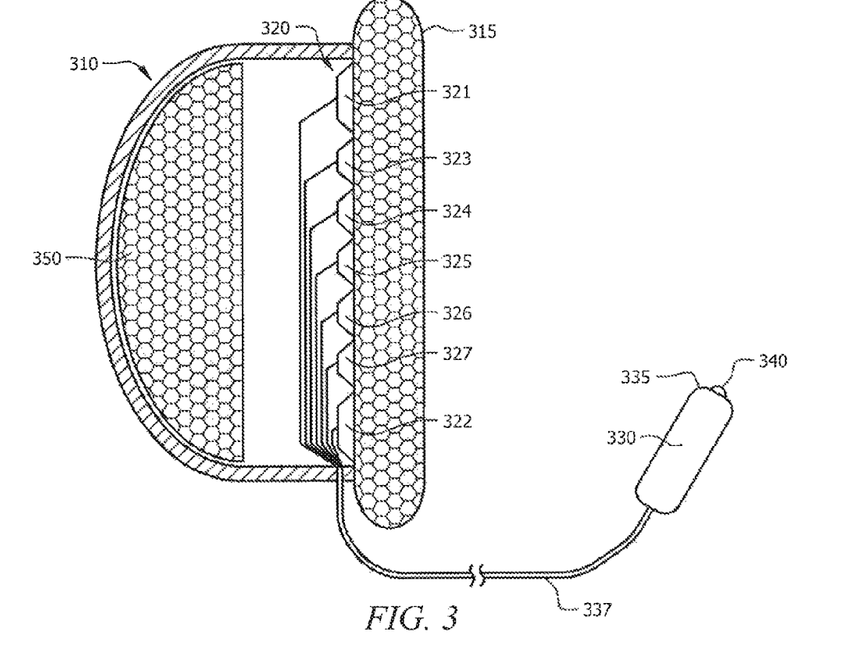
FIG. 3 illustrates schematically a cross-section of an alternate embodiment of an improved ear cup (in which the microphone and active noise cancellation circuitry are located external and apart from the earcup)

In some embodiments, the active noise cancellation circuitry would be located within the earcup (for example, in the airspace behind the speaker array), and the external microphone would be located on the exterior surface of the earcup (and would transmit the detected external noise/sound signal to the active noise cancellation circuitry). Typically, a wire (for transmitting the detected sound from the microphone to the circuitry) would run through the earcup (e.g. extending through the earcup shell wall), but this location would be sealed such that the internal airspace of the earcup would not be connected to the external environment airspace. In other embodiments, the active noise cancellation circuitry and/or microphone could be located external from the earcup shell and separate and apart from the earcup shell. For example, FIG. 3 illustrates an exemplary embodiment in which both the active noise cancellation circuitry and microphone are located in a separate, external housing. And as mentioned above, in some embodiments the earcup would be a standalone unit, operable to be used with various off-the-shelf active noise cancellation systems (which for example, might include the active noise cancellation circuitry and external microphone and provide (for example, via a standard jack electrical attachment) an output signal). In such embodiments using off-the-shelf active noise cancellation systems, the earcup would typically include one frequency filter for each speaker and/or one amplifier for each speaker.

The earcup embodiments typically provide active noise cancellation, and embodiments often may also provide passive hearing protection/attenuation, with the combination of passive and active hearing protection providing improved total hearing protection. To provide passive hearing protection, the earcup may further comprise an airspace (e.g. open volume of air, for ex. 100,000-300,000 cubic millimeters volume) and/or sound absorbing foam (e.g. reticulated and/or non-reticulated foam with thickness ranging from 1 mm up to the entire open volume of the cup). In some embodiments, the earcup may also comprise a sealing section, operable to seal the user's ear canal (for better passive noise reduction). Typically, the earcup may provide at least passive Noise Reduction Ratting (NRR) of 20 or 25 by sealing a user's ear canal with the earcup.

Figure 2:
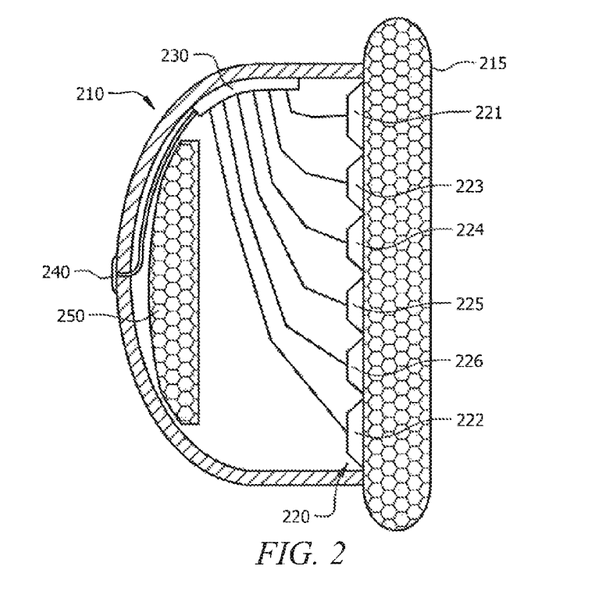
FIG. 2 illustrates schematically a cross-section of an embodiment of an improved earcup, comprising a speaker array having multiple speakers in each ear cup.

FIG. 2 illustrates an exemplary earcup 210 (similar to embodiments described above), having an optional sealing section (such as an air or foam cushion) 215 located along the circumference of the open edge of the hollow earcup shell 210. An array of speakers 220 is located within the earcup 210, with each of the plurality of speakers typically oriented outward (for example, to direct sound into the user's ear canal when the earcup 210 is in place on the user's head). Typically, the plurality of speakers of the speaker array would all be located in the same plane within the earcup, with each such speaker facing the user's ear (when the earcup is worn). So, a retaining frame might position the plurality of speakers in a single plane within the earcup (e.g. holding the speakers in a single plane). The speaker array 220 of FIG. 2 comprises a plurality of speakers (and while two or more speakers could be used, in FIG. 2 for example 6 speakers 221, 222, 223, 224, 225, 226 are used). In FIG. 2, two of the speakers are larger speakers 221, 222 (which might for example be 40-50 mm and be assigned to handle the lower frequency ranges), while the remaining speakers 223, 224, 225, 226 are smaller speakers (which might for example be 5 mm and be assigned to handle the remaining/upper frequency ranges). It should be understood that the specific number of speakers and sizes of speakers shown for FIG. 2 are merely illustrative, and therefore are not limiting. For example, in other embodiments, each earcup might have three speakers, with one speaker assigned to high frequency range, one speaker assigned to mid frequency range, and one speaker assigned to low frequency range (for example, a 5 mm speaker might be assigned to 10,000-15,000 Hz, a 15-20 mm speaker might be assigned to 3,000-10,000 Hz, and a 40-50 mm speaker might be assigned to 20-3,000 Hz). And in other embodiments, more than one such speaker might be assigned to any one (or all) of the frequency ranges.

The earcup 210 for the embodiment of FIG. 2 also includes an active noise cancellation circuitry 230 and an external microphone 240. In FIG. 2, the external microphone 240 is attached to the external surface of the earcup 210, and a wire (or other transmission means) penetrates the earcup 210 and connects to the active noise cancellation circuitry 230, allowing the detected noise/sound from the microphone to be transmitted to the circuitry 230 for processing. The active noise cancellation circuitry 230 is then connected (for example, via wires or other transmission means) to each of the speakers in the speaker array 220. Additionally, the earcup 210 of FIG. 2 contains a foam element 250 to aid in sound absorption (for passive noise protection). FIG. 2 is merely illustrative, and variants as described in embodiments above are understood to be within this disclosure.

FIG. 3 illustrates a similar embodiment, in which the external microphone and active noise cancellation circuitry are located outside, separate and apart from the earcup. So in FIG. 3, the earcup 310 comprises the speaker array 320 (having a plurality of speakers, for example speakers 321, 322, 323, 324, 325, 326, 327) and sound absorbing foam 350 (typically along with sealing section 315). The external microphone 340 (for detecting external sound/noise) and active noise cancellation circuitry 330 in FIG. 3 are not located within the earcup, but rather may be located in/on a separate housing 335 (or in some other embodiments, they may be located in a separate earcup, which may serve as the separate housing). Typically, a wire or other transmission means 337 would connect the active noise cancellation circuitry 330 to the speaker array 320.

In headphone or earmuff embodiments having two earcups (one for each ear of the user), some of the elements described above might be associated with only one earcup (for example, the two earcups might share some elements, as discussed above with respect to FIG. 3, for example). So for example, each earcup might include a speaker array, but there might be only a single external microphone and a single active noise cancellation/reduction circuitry to be shared between the two earcups. Additionally, some embodiments might not actually include an earcup (but otherwise be similar to the various embodiments described above), for example being earbuds or headphones that do not seal the user's ear canal but which fit over or within the ear canal opening so that the speaker array may provide active noise cancellation to the user's ears. While such embodiments without passive hearing protection would likely not be as effective for hearing protection, they still may meet a user's needs in certain circumstances (for example, when the noise environment is not especially damaging or dangerous).

The speaker array of the disclosed embodiments typically would be used for improved active noise reduction. For example, the speaker array may particularly allow for cancellation of frequencies in the lower frequency ranges (since these are the frequency ranges that standard, one speaker devices typically have most difficulty with), leading to better noise cancellation ability. In other embodiments, the speaker array may achieve a wider range of sound reproduction within the earcup on both the upper and lower spectrum of frequencies. In still other embodiment, each speaker in the array could be configured/selected to better target its specific narrow frequency range (for example, providing good/better fidelity). And depending on the resonant frequencies of the speakers, the speaker array could provide higher NRR through the use of speakers with lower or higher resonant frequencies than a single speaker. For example, an array of speakers would typically have several resonant frequencies, which would all be at a lower level (unlike an earcup with only one speaker, which would typically have only one resonant frequency at a higher level). This can be significant in the hearing protection context, since it may allow the resonance to be distributed over the frequency range instead of being concentrated. Thus, the presently disclosed earcups having a speaker array (with a plurality of speakers) may deliver a more balanced noise reduction curve over the frequency range. In addition to the active noise cancellation features/uses, the disclosed embodiments might also be used to provide improved music or communication capabilities in the earcup (for example, via a plug/port/electrical attachment operable to connect to an external unit). For example, the speaker array could provide enhanced audio performance, with higher/better fidelity. Such non-noise cancellation uses would typically function better due to active noise cancellation (since the noise cancellation would reduce background noise which might interfere with hearing the other uses). So, the speaker array may be capable of providing both active noise cancellation and one or more of the non-cancellation uses simultaneously.

Figure 4:
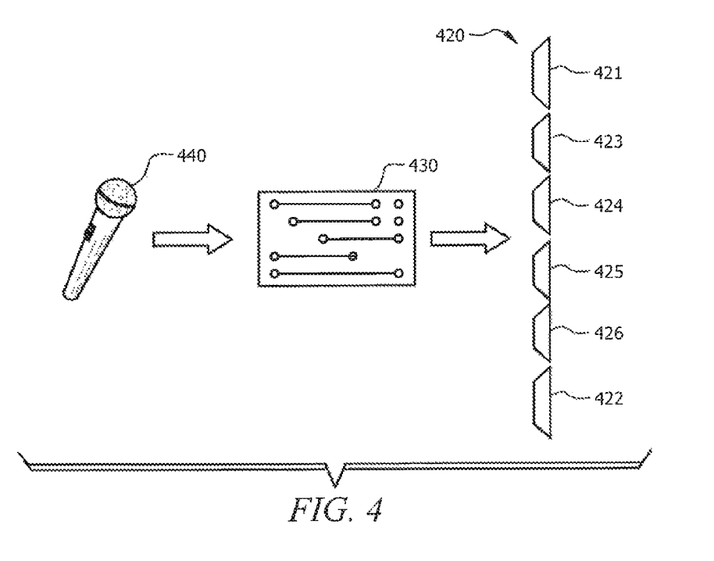
FIG. 4 illustrates schematically the interaction of elements for an improved method of active noise cancellation.

Some embodiments of the disclosure may comprise methods of using such devices for active noise cancellation/reduction. For example, a method for using an earcup (or other such device) having an array of speakers for noise reduction, may comprise the steps of detecting external sound (for example, using an external microphone), generating an active noise cancellation signal based on the detected external sound (for example, using active noise cancellation circuitry), and transmitting the signal to the array of speakers within the earcup, with the array of speakers providing active noise cancellation over a total frequency range; the array of speakers comprising a plurality of speakers; and each speaker providing active noise cancellation for a narrow frequency range which is a portion of the total frequency range. FIG. 4 illustrates schematically such an exemplary method, with the external microphone 440 detecting noise/sound external to the earcup/user's ear and transmitting the sound to the active noise cancellation circuitry 430. The circuitry 430 then generates an output signal to each of the speakers 421, 422, 423, 424, 425, 426 (which are merely exemplary in size and number) in the speaker array 420, for transmission of the active noise cancellation signal into the user's ear canal.

In some embodiments, generating an active noise cancellation signal might comprise: active noise reduction circuitry receiving a signal for detected external sound from an external microphone; the active noise reduction circuitry generating an output signal for active noise cancellation based on the detected external sound (which might typically include inverting the detected external noise/sound signal from the microphone); and/or the active noise cancellation circuitry dividing the resulting active noise cancellation output signal into frequency range bands for transmission, with each frequency range band corresponding to a specific speaker having a corresponding narrow frequency range. In some embodiments, the active noise cancellation circuitry might use frequency filters and amplifiers (for example, one frequency filter and one amplifier for each speaker in the array) in preparing the output signal to the speaker array, for example filtering the frequency into the narrow frequency ranges and amplifying each such filtered signal prior to transmission to the corresponding speaker.

Figure 5:
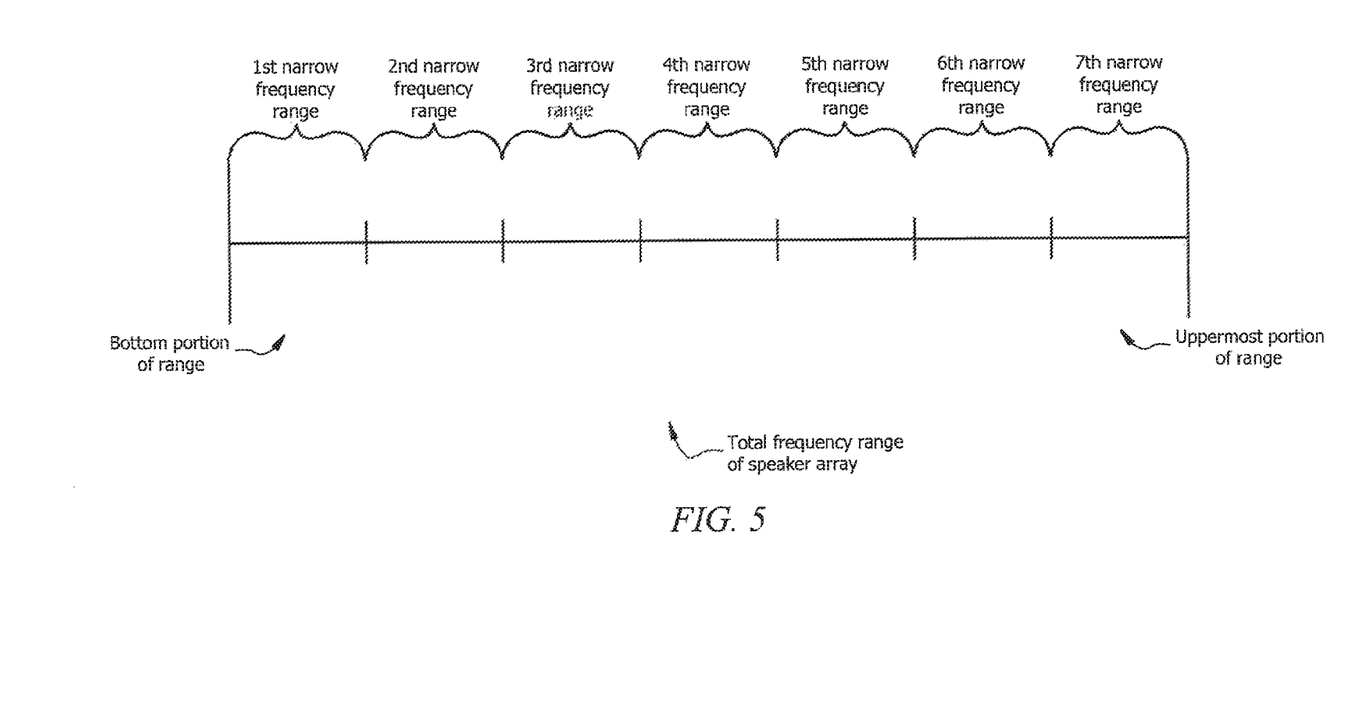
FIG. 5 illustrates schematically the total frequency range of an exemplary speaker array, along with the narrow frequency ranges assigned to the plurality of speakers in the speaker array.

FIG. 5 schematically illustrates an exemplary total frequency range for an exemplary speaker array, in which the total frequency range is divided into a plurality (for example seven in the illustration of FIG. 5) narrow frequency ranges corresponding for example to a corresponding number (for example, seven in the illustration of FIG. 5) different speakers (each of which would typically be configured to reproduce the designated narrow frequency range with high fidelity). In another illustrative embodiment, the total frequency range (for example from 20 Hz to 15,000-20,000 Hz) may be divided into three narrow frequency ranges corresponding to three different speakers (for example, with a 5 mm speaker being assigned to transmit frequencies from about 10,000-15,000 Hz, a 15-20 mm speaker being assigned to transmit frequencies from about 3,000-10,000 Hz, and a 40-50 mm speaker being assigned to transmit frequencies from about 20-3,000 Hz). It is to be understood, however, that the number of narrow frequency ranges and the number of and/or size of speakers may vary depending on the embodiments (so long as the number of narrow frequency ranges matches the number of speakers in the speaker array, and the number represents a plurality, for example). The plurality of speakers of the speaker array typically would comprise speakers of varying sizes and/or resonant frequencies (for example, with at least one speaker being approximately 40-50 mm, and with at least one other speaker being approximately 5 mm), such that each speaker would be configured to maximize sound reproduction/quality/fidelity within its corresponding narrow frequency range. Some method embodiments would include selecting or configuring speakers for the speaker array in order to match specific speaker performance with the assigned/corresponding narrow frequency range for each speaker (e.g. selecting or configuring specific speakers to ensure that each speaker will have good characteristics for reproduction in the assigned/corresponding narrow frequency range). And in some embodiments, the total frequency range of the speaker array would cover approximately the entire range of human hearing. Some method embodiments would also include providing at least passive NRR of 25 (for example a range from about 20 to 30 NRR) by sealing a user's ear canal with the earcup.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented. And logic flows for methods do not necessarily require the particular order shown, or sequential order, to achieve desirable results. Other steps may be provided, or steps may be eliminated, from the described flows/methods, and other components may be added to, or removed from, the described devices/systems. So, other embodiments may be within the scope of the following claims.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An earcup comprising:
   a hollow cup shell operable to enclose a user's ear canal and to provide passive noise reduction;
   an array of speakers within the cup shell;
   an external microphone operable to detect noise external to the cup shell; and
   active noise cancellation circuitry;
   wherein:
   the array of speakers and the active noise cancellation circuitry are configured to provide active noise cancellation over a total frequency range, wherein the total frequency range comprises approximately an entire range of human hearing;
   the array of speakers comprising a plurality of speakers;

each speaker is configured to provide active noise cancellation for a narrow frequency range which is a portion of the total frequency range;

the active noise cancellation circuitry is configured to receive a signal for detected external noise from the external microphone, and is operable to generate an output signal for active noise cancellation based on the detected external noise; and the active noise cancellation circuitry is configured to divide the resulting active noise cancellation output signal into frequency range bands for transmission, with each frequency range band corresponding to a specific speaker having a corresponding narrow frequency range.

2. The earcup of claim 1, wherein the active noise cancellation circuitry is configured to generate the output signal for active noise cancellation by inversion of the detected external noise from the microphone.

3. The earcup of claim 1, wherein the cup shell comprises a sealing section operable to seal the user's ear canal for passive noise reduction.

4. The earcup of claim 3, further comprising an airspace and sound absorbing foam.

5. The earcup of claim 1, wherein the active noise cancellation circuitry and microphone are located external from the cup shell and separate and apart from the cup shell.

6. The earcup of claim 1, wherein the plurality of speakers comprise speakers of varying sizes and resonant frequencies.

7. The earcup of claim 6, wherein at least one of the plurality of speakers is a 40-50 mm speaker with a narrow frequency range corresponding to the bottom portion of the total frequency range; and wherein at least one of the plurality of speakers is a 5 mm speaker with a narrow frequency range corresponding to the uppermost portion of the total frequency range.

8. The earcup of claim 1, wherein each of the plurality of speakers is configured to maximize sound reproduction within its corresponding narrow frequency range.

9. A device for active noise cancellation, comprising:
a hollow earcup operable to enclose a user s ear canal and to provide passive noise reduction;
an array of speakers within the earcup;
a microphone; and
active noise cancellation circuitry;
wherein:
the array of speakers and the active noise cancellation circuitry are configured to provide active noise cancellation over a total frequency range, wherein the total frequency range comprises approximately an entire range of human hearing;
the array of speakers comprises a plurality of speakers;
each speaker is configured to provide active noise cancellation for a narrow frequency range which is a portion of the total frequency range;
the active noise cancellation circuitry is configured to receive a signal for detected noise from the microphone, and is operable to generate an output signal for active noise cancellation based on the detected noise; and
the active noise cancellation circuitry is configured to divide the resulting active noise cancellation output signal into frequency range bands for transmission, with each frequency band corresponding to a specific speaker having a corresponding narrow frequency range.

10. The device of claim 9, wherein the earcup comprises a sealing section operable to seal the user's ear canal.

11. The device of claim 9, wherein each of the plurality of speakers is configured to maximize reproduction within its corresponding narrow frequency range.

12. The device of claim 9, wherein at least one of the plurality of speakers is a 40-50 mm speaker with a narrow frequency range corresponding to the bottom portion of the total frequency range; and wherein at least one of the plurality of speakers is a 5 mm speaker with a narrow frequency range corresponding to the uppermost portion of the total frequency range.

13. A device for active noise cancellation, comprising:
a hollow earcup operable to enclose a user's ear canal and to provide passive noise reduction;
an array of speaker within the earcup;
an external microphone operable to detect noise external to the earcup; and
active noise cancellation circuitry;
wherein:
the array of speakers and the active noise cancellation circuitry are configured to provide active noise cancellation over a total frequency range, wherein the total frequency range comprises approximately an entire range of human hearing;
the array of speakers comprises a plurality of speakers;
each speaker is configured to provide active noise cancellation for a narrow frequency range which is a portion of the total frequency range;
the active noise cancellation circuitry is configured to receive a signal for detected external noise from the external microphone, and is operable to generate an output signal for active noise cancellation based on the detected external noise; and
the active noise cancellation circuitry is configured to divide the resulting active noise cancellation output signal into frequency range bands for transmission, with each frequency range band corresponding to a specific speaker having a corresponding narrow frequency range.

14. A method for noise reduction in an earcup, with the earcup having an array of speakers, comprising the steps of:
detecting external sound;
generating an active noise cancellation signal based on the detected external sound;
transmitting the active noise cancellation signal to the array of speakers within the earcup;
wherein the transmitting step comprises:
providing, by the array of speakers, the transmitted active noise cancellation signal over a total frequency range, wherein the total frequency range comprises approximately an entire range of human hearing, and wherein the array of speakers comprises a plurality of speakers; and
wherein each of the speakers of the array speakers provides the transmitted active noise cancellation signal corresponding a narrow frequency range which is a portion of the total frequency range.

15. The method of claim 14, wherein the detecting step comprises:
receiving, by active noise cancellation circuitry, a signal from an external microphone to detect the external sound; and
wherein the generating step comprises:
generating, by the active noise cancellation circuitry, an output signal for active noise cancellation based on the detected external sound; and dividing, by the active noise cancellation circuitry, the active noise cancellation output signal into frequency range bands for transmission, with each frequency range band corresponding to a specific speaker having a corresponding narrow frequency range.

16. The method of claim 14, further comprising providing at least passive Noise Reduction Rating (NRR) of 25 by sealing a user's ear canal with the earcup.

17. The method of claim 14, further comprising configuring each speaker to maximize sound reproduction within its corresponding narrow frequency range.

18. The method of claim 14, wherein the total frequency range comprises approximately an entire range of human hearing.

* * * * *

UNITED STATES PATENT AND TRADEMARK OFFICE
CERTIFICATE OF CORRECTION

PATENT NO.        : 9,786,261 B2
APPLICATION NO.   : 14/571031
DATED             : October 10, 2017
INVENTOR(S)       : John Jenkins Page 1 of 1

It is certified that error appears in the above-identified patent and that said Letters Patent is hereby corrected as shown below:

In the Claims

Column 8, Line 67: "comprising" should be "comprises"

Column 9, Line 41: "user s" should be "user's"

Column 9, Line 64: insert the word --range-- after "frequency"

Column 10, Line 16: "speaker" should be "speakers"

Column 10, Line 46: delete "active noise cancellation"

Column 10, Line 49: delete "the transmitted"

Column 10, Line 50: delete "signal"

Column 10, Line 55: delete "wherein" and replace with "providing, by"

Column 10, Line 55: "array speakers" should be "array of speakers,"

Column 10, Line 55: delete "provides the transmitted"

Column 10, Line 56: delete "signal"

Column 10, Line 57: delete "corresponding" and replace with "for"

Signed and Sealed this
Second Day of January, 2018

Joseph Matal
*Performing the Functions and Duties of the
Under Secretary of Commerce for Intellectual Property and
Director of the United States Patent and Trademark Office*